(12) United States Patent
Villarreal

(10) Patent No.: US 7,230,688 B1
(45) Date of Patent: Jun. 12, 2007

(54) SYSTEM AND METHOD FOR PROCESSING INFORMATION IN A PULSE OXIMETER

(75) Inventor: Richard A. Villarreal, West Richland, WA (US)

(73) Assignee: Cadwell Industries, Inc., Kennewick, WA (US)

( * ) Notice: Subject to any disclaimer, the term of this patent is extended or adjusted under 35 U.S.C. 154(b) by 305 days.

(21) Appl. No.: 10/780,277

(22) Filed: Feb. 17, 2004

Related U.S. Application Data

(60) Provisional application No. 60/448,182, filed on Feb. 14, 2003.

(51) Int. Cl.
    *G01N 33/48* (2006.01)
(52) U.S. Cl. .................. 356/41; 250/206; 250/564; 600/300; 600/323
(58) Field of Classification Search .............. 356/41, 356/40, 42; 600/300, 310, 323; 250/214.1, 250/214 R, 206, 564
See application file for complete search history.

(56) References Cited

U.S. PATENT DOCUMENTS

| | | | | |
|---|---|---|---|---|
| 4,781,195 A | * | 11/1988 | Martin | .................. 600/336 |
| 6,011,986 A | * | 1/2000 | Diab et al. | .................. 600/323 |
| 6,397,091 B2 | * | 5/2002 | Diab et al. | .................. 600/323 |
| 6,515,273 B2 | * | 2/2003 | Al-Ali | .................. 250/214.1 |
| 6,825,619 B2 | * | 11/2004 | Norris | .................. 315/149 |
| 6,993,371 B2 | * | 1/2006 | Kiani et al. | .................. 600/323 |

\* cited by examiner

*Primary Examiner*—Layla G. Lauchman
(74) *Attorney, Agent, or Firm*—Christensen O'Connor Johnson Kindness PLLC

(57) ABSTRACT

A pulse oximeter for measuring arterial oxygen saturation levels is provided. The pulse oximeter includes an LED signal generator for transmitting one or more light signals to a testing medium and a photodetector signal generator for processing at least a portion of the light signal generated by the LED signal generator into a photocurrent. The pulse oximeter further includes an integrated information transmission component for transmitting information corresponding to the pulse oximeter and which is integrated with the pulse oximeter without requiring additional wiring. A processing system within the pulse oximeter can generate a voltage to the integrated information transmission component to read the information stored in the component without causing the LED signal generator to generate a signal.

26 Claims, 4 Drawing Sheets

SYSTEM AND METHOD FOR PROCESSING INFORMATION IN A PULSE OXIMETER

CROSS-REFERENCE TO RELATED APPLICATION

This application claims the benefit of U.S. Provisional Application No. 60/448,182 entitled MEDICAL DEVICE AND INFORMATION PROCESSING SYSTEMS, and filed on Feb. 14, 2003. U.S. Provisional Application No. 60/448,182 is incorporated by reference herein.

FIELD OF THE INVENTION

In general the present invention relates to medical devices, and in particular, to a system and method for transmitting information in pulse oximeters.

BACKGROUND OF THE INVENTION

Generally described, pulse oximetry is used to continuously monitor the arterial blood saturation of a patient in a variety of monitoring environments, such as hospitals, clinics, or for home use. Conventional pulse oximeters use two wavelengths of light generated from light emitting diodes (LEDs) that are transmitted into a pulsatile tissue bed corresponding to a tested subject. Generally described, for estimating oxygen saturation in the bloodstream, at least one of the LED's primary wavelength must be chosen at some point in the electromagnetic spectrum such that the absorption of oxyhemoglobin ($HbO_2$) differs from the absorption of reduced hemoglobin (Hb). The second LED's primary wavelength is then chosen at some point within the electromagnetic spectrum such that the absorption of Hb and $HbO_2$ are different from the absorption of the first LED. One skilled in the relevant art will appreciate that commercial pulse oximeters typically utilize one LED whose wavelength in the near red part of the electromagnetic spectrum near 660 nanometers. Additionally, the typical commercial pulse oximeter has a second LED whose wavelength is in the near infrared part of the electromagnetic spectrum.

The emitted light signals are collected by a photodiode, which processes the light signals into photocurrents. The photocurrents can be processed to measure a modulation ratio of the red, or near red signal, to the infrared, or near infrared signal. The modulation ratio then corresponds to arterial oxygen saturation ($SaO_2$).

To properly calculate $SaO_2$ levels, the wavelength of the LED's must be precisely known. One approach to transmit LED wavelength information utilizes a resistor with the pulse oximeter probe that has a value indicative of the wavelength of the LED. The resistor value of the LED is then used to code the transmission LEDs. The oximeter can read the resistor value and utilize the value of the resistor to calculate the $SaO_2$ value. An example of a system utilizing this approach can be found in U.S. Pat. No. 4,621,643, assigned to Nellcor, Inc. Although this approach allows for increased tuning, the approach can become deficient in that it typically requires separate electrical connections to read the resistor value. Because each separate electrical connection increases the overall cost of the unit, this approach is not cost effective.

Another approach to improve the transmission of LED wavelength information also utilizes a resistor having a value indicative of the wavelength of the LED. However, this approach places the resistor in parallel to the LED so that it does not significantly add to the cost of the pulse oximeter. By providing a current that does not enable the LED, an oximeter can read the information from the parallel resistor and process the wavelength information. An example of a pulse oximeter utilizing this approach can be found in U.S. Pat. No. 6,011,986. However, this approach is typically limited in that the dynamic range of reading voltages can never exceed the turn on voltage of the LED. For example, this approach can be limited to the utilization of resistors because other identification devices cannot typically operate at a level below the operating voltage of the LED.

Thus, there is a need for a pulse oximeter configuration that can transmit information corresponding to the operation of the pulse oximeter without requiring additional wiring components and/or that allows for a full range of reading environments.

SUMMARY OF THE INVENTION

A pulse oximeter for measuring arterial oxygen saturation levels is provided. The pulse oximeter includes an LED signal generator for transmitting one or more light signals to a testing medium and a photodetector signal generator for processing at least a portion of the light signal generated by the LED signal generator into a photocurrent. The pulse oximeter further includes an integrated information transmission component for transmitting information corresponding to the pulse oximeter and which is integrated with the pulse oximeter without requiring additional wiring. A processing system within the pulse oximeter can generate a voltage to the integrated information transmission component to read the information stored in the component without causing the LED signal generator to generate a signal.

In accordance with an aspect of the present invention, a pulse oximeter for measuring arterial oxygen saturation levels is provided. The pulse oximeter includes an LED signal generator for transmitting one or more light signals to a testing medium and a photodetector signal generator for obtaining at least a portion of the light signal generated by the LED signal generator and for generating a photocurrent corresponding to the detected signals. The pulse oximeter further includes an integrated information transmission component for storing information corresponding to the pulse oximeter and for transmitting the information. Still further, the pulse oximeter includes an oximeter processing system for causing the LED signal generator to generate a signal, for processing the photocurrent from the photodetector signal generator and for providing a voltage source to cause the information transmission component to transmit the stored information corresponding to the pulse oximeter. The voltage source provided by the oximeter processing system to read the information transmission component can be higher than a turn on voltage for the LED signal generator without causing the LED signal generator to generate a signal.

In accordance with another aspect of the present invention, a pulse oximeter for measuring arterial oxygen saturation levels is provided. The pulse oximeter includes a signal generator for transmitting one or more signals to a testing medium and a photodetector signal generator for processing at least a portion of the signal generated by the signal generator. The pulse oximeter further includes an integrated information transmission component for storing information corresponding to the pulse oximeter and for transmitting the information. The integrated information transmission component is configured to not require additional wiring to be integrated in the pulse oximeter. The pulse oximeter further includes an oximeter processing system in communication with the signal generator, the photodetector signal generator and the integrated information transmission component. The oximeter processing system provides voltage to cause the information transmission component to transmit the stored information corresponding to the pulse oximeter. The voltage source can be higher than a turn on voltage for the signal generator without causing the signal generator to generate a signal.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Generally described, the present invention relates to an apparatus for measuring arterial oxygen saturation ($SaO_2$) levels by including the transmission of various information corresponding to characteristics of a probe. More specifically, the present invention corresponds to a configuration of an apparatus, such as a pulse oximeter, that can include the transmission of information corresponding to one or more characteristics of a probe in a cost effective manner. As described with regard to the present invention, information can include data corresponding aspects of the components of an oximeter, such as data identifying the precise wavelength of the LEDs, dates of manufacturer, an identification of a manufacturer, authentication codes and/or serial numbers. Additionally, the transmitted information can also include data to be utilized by the oximeters, such as software programs, updates, patient identification information, clinic identification information and the like. Although the present invention will be described with regard to pulse oximeters, probes and other identified components, one skilled in the relevant art will appreciate that the disclosed embodiments are illustrative in nature and should not be construed as limiting. Further, one skilled in the relevant art will appreciate that various components of the illustrative medical device and/or the processes/information associated with its operation may vary with the implementation of the present invention beyond pulse oximeters.

Figure 1:
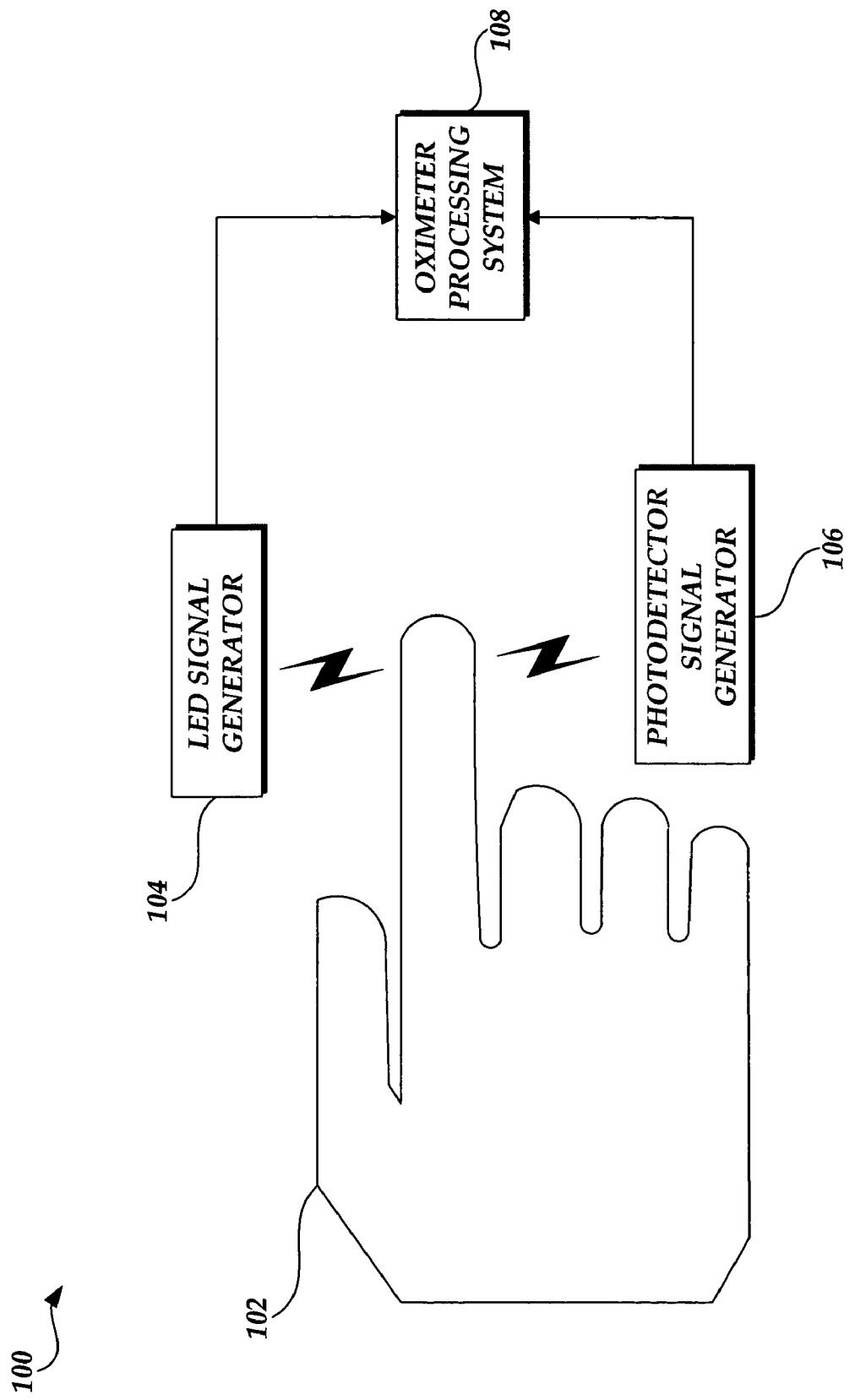
FIG. 1 is a block diagram illustrative of a pulse oximeter system for measuring arterial oxygen saturation levels in a medium in accordance with the present invention

In an illustrative embodiment of the present invention, the medical device of the present invention is embodied as a pulse oximeter. FIG. 1 is a block diagram illustrative of a pulse oximeter system 100 utilized in accordance with the present invention. The pulse oximeter system includes a medium 102 for measuring arterial oxygen saturation such as a finger or earlobe. The pulse oximeter system 100 also includes an LED signal generator 104 that can include one or more LEDs for transmitting light. The pulse oximeter system 100 further includes a photodetector signal generator 106 for absorbing the light from the LED signal generator 104 as it passes through the medium 102 and for generating a signal corresponding to the detected light. The pulse oximeter system 100 also includes an oximeter processing system 108 for controlling the generation of the light from the LED signal generator 104 and for processing the signals generated by photodetector signal generator 106. One skilled in the present invention will appreciate that the medium 102 will absorb and scatter a particular wavelength of light depending on the characteristics of the medium. Based on this principle, the oximeter processing system 108 can then calculate the arterial oxygen saturation of the tested medium. The function of pulse oximeters is well known in the present art and will not be described in greater detail.

Figure 2:
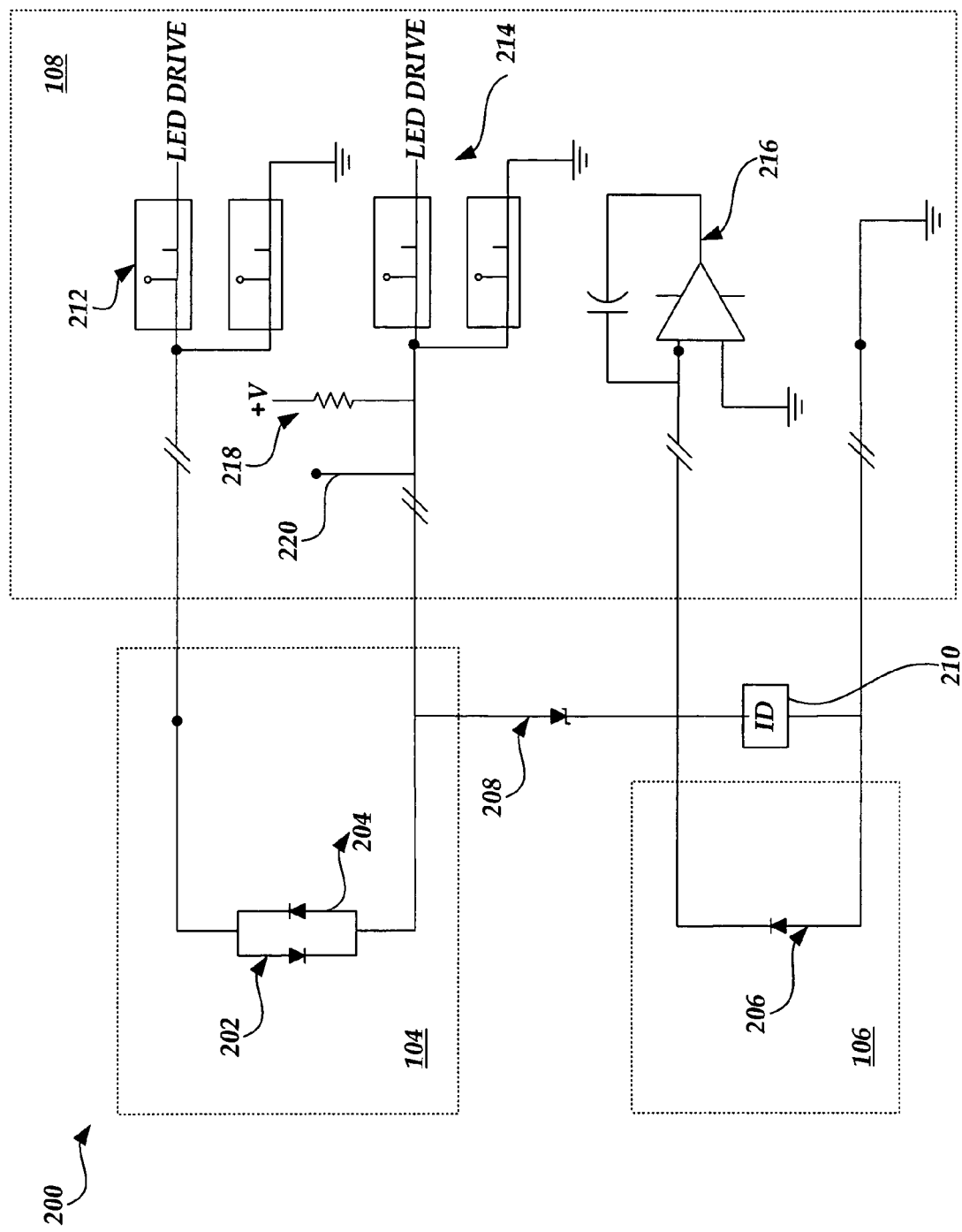
FIG. 2 is a circuit diagram implemented with a pulse oximeter system for measuring arterial oxygen saturation levels in a medium in accordance with the present invention.

With reference now to FIG. 2, an illustrative circuit 200 of a pulse oximeter system 100 (FIG. 1) for implementing the information transmitting function of the present invention will be described. The circuit 200 includes an LED signal generator 104 that includes two parallel LEDs 202, 204. In an illustrative embodiment of the present invention, each LED 202, 204 corresponds to a different wavelength of light. For example, one LED may correspond to a wavelength in the red, or near red, light on the electromagnetic spectrum while another LED may correspond to a wavelength in the infrared, or near infrared, light on the electromagnetic spectrum. The circuit 200 also includes a photodetector signal generator 106 that includes a photodetector 206 that receives light generated by the LEDs 202, 204 and generates a photocurrent corresponding to the detected light. The photodetector 206 and the LEDs 202, 204 are connected electrically in parallel. Further, as illustrated in FIG. 2, a schottkey diode 208 is also connected in parallel to the LEDs 202, 204 and the photodetector 206.

The circuit 200 also includes an information transmission component 210 in which information may be stored and read. In an illustrative embodiment of the present invention, the information transmission component 210 may be embodied in a permanent storage media such that the information cannot be modified or additional information may not be stored in the component. Additionally, all, or a portion, of the information transmission component 210 may be embodied in a writable, permanent storage media such that some information may be added to the component. Alternatively, the information transmission component 210 may be embodied in a writable, nonpermanent storage media such that some or all of the information may be overwritten. An example of an information storage component 210 can include an identification chip, such as the Dallas Semiconductor DS 1990 or DS 2401. Another example of an information storage component 210 can include electrical components, such as a resistor, whose characteristics have a value that corresponds to information. For example, the resistive value of a resistor may correspond to the precise wavelength of an LED 202, 204. As illustrated in FIG. 2, the information transmission component is configured in parallel to the photodetector 206 and does not require additional wiring to be connected to the circuit 200.

The circuit 200 also includes an oximeter processing system 108 that is utilized to drive the LED signal generator 104 and process signals coming from the photodetector signal generator 106. The oximeter processing system 108 also generates a signal that can cause the information transmission component 210 to transmit information to be processed by the oximeter processing system. The oximeter processing system 108 includes two sets of switches 212, 214 which are connected to LED drivers for causing the LEDs 202, 204 to generate light. The oximeter processing system 108 also includes a filter 216 for processing the signal from the photodetector 206, which is further transmitted to a microprocessor (not shown) for determining the arterial oxygen saturation of the medium 102. One skilled in the relevant art will appreciate that these components are well known for use in the function of pulse oximeters and will not be described in greater detail. The oximeter processing system 108 also includes a separate voltage source 218 for driving the information transmission component 210. In an illustrative embodiment of the present invention, the separate voltage source 218 provides a voltage less than the turn on voltage for the LEDs 202, 204. However, although the voltage source 218 is illustrated as separate, one skilled in the relevant art will appreciate that the voltage source 218 may be integrated with other components, such as switches 212 or 214.

In practice, to read the information from the identification transmission component 210, switches 212, 214 are opened. With the branch corresponding to the LED open, the voltage from the separate voltage source 218 passes through schottkey diode 208 and to the information processing component 210. The resulting voltage drop across the resistor can be read at 220, which corresponds to the value generating by the information transmission component 210. The value detected at 220 can be transmitted to a microprocessor (not shown) for further processing. For example, if the information transmission component 210 transmits information regarding the precise wavelength information for one or more LEDs 202, 204, the processor can utilize the wavelength information to calculate the arterial oxygen saturation level of the medium 102. Alternatively, if the information transmission component 210 transmits information regarding a certificate of authenticity, the processor can use the information to verify operation and/or register the component with the manufacturer.

Figure 3:
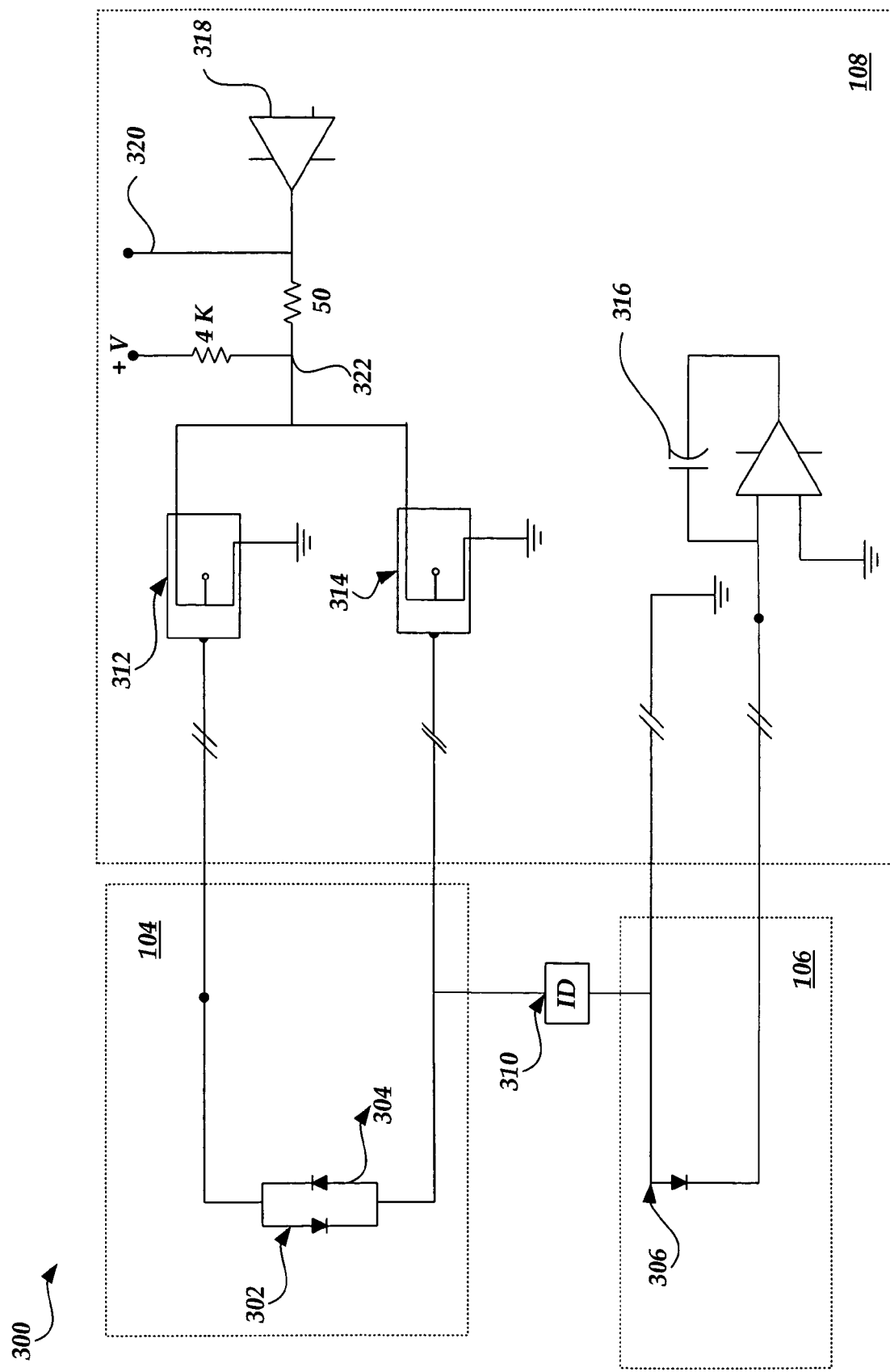
FIG. 3 is a circuit diagram implemented with a pulse oximeter system for measuring arterial oxygen saturation levels in a medium in accordance with the present invention.

With reference now to FIG. 3, an alternative illustrative circuit 300 of a pulse oximeter system 100. (FIG. 1) for implementing the information transmitting function of the present invention will be described. The circuit 300 includes an LED signal generator 104 that includes two parallel LEDs 302, 304. Similar to above-described circuit 200 (FIG. 2), each LED 302, 304 corresponds to a different wavelength of light. For example, one LED may correspond to a wavelength in the red, or near red, light on the electromagnetic spectrum while another LED may correspond to a wavelength in the infrared, or near infrared, light on the electromagnetic spectrum. The circuit 300 also includes a photodetector signal generator 106 that includes a photodetector 306 that receives light generated by the LEDs 302, 304 and generates a photocurrent corresponding to the detected light.

The circuit 300 also includes an information transmission component 310 in which information may be stored and read. Similar to the information transmission component 210 (FIG. 2), the information transmission component 310 may be embodied in a permanent storage media such that the information cannot be modified or additional information may not be stored in the component. Additionally, all, or a portion, of the information transmission component 310 may be embodied in a writable, permanent storage media such that some information may be added to the component. Alternatively, the information transmission component 310 may be embodied in a writable, nonpermanent storage media such that some or all of the information may be overwritten. An example of an information transmission component 310 can include an identification chip, such as the Dallas Semiconductor DS 1990 or DS 2401. As illustrated in FIG. 3, the information transmission component is connected to the anode of photodetector 306, the cathode of LED 302, and anode of LED 304, and does not require additional wiring to be connected to the circuit 300.

The circuit 300 also includes an oximeter processing system 108 that is utilized to drive the LED signal generator 104 and process signals coming from the photodetector signal generator 106. The oximeter processing system 108 also generates a signal that can cause the information transmission component 310 to transmit information to be processed by the oximeter processing system. The oximeter processing system 108 includes two sets of switches 312, 314 which are connected to either an LED drive for causing the LEDs 302, 304 to generate light or a ground to allow no current to flow. The oximeter processing system 108 also includes a filter 316 for processing the signal from the photodetector 306, which is further transmitted to a microprocessor (not shown) for determining the arterial oxygen saturation of the medium 102. One skilled in the relevant art will appreciate that these components are well known for use in the function of pulse oximeters and will not be described in greater detail. The oximeter processing system 108 further includes an operational amplifier 318 and two nodes 320, 322 that are utilized to sense current that is flowing through the LEDs 302, 304. The two nodes 320, 322 will also be utilized to provide a power source to the information transmission component 310 and to read the information transmitted from the information transmission component, as will be explained in greater detail below. As illustrated in FIG. 3, node 320 may include an additional resistor connected in series.

In practice, to read the information from the identification transmission component 310, switches 312, 314 are connected to allow current to flow through to the LEDs. Unlike circuit 200, the switches 312, 314 are not left in an open position. Additionally, operation amplifier 318 is shut down, such that it presents high impedance to the circuit 300. Further, node 322 is connected to a power source and node 320 is connected to a microprocessor for reading information from the identification transmission component 310. Node 320 may already be connected to a microprocessor for monitoring current sent to the LED during operation of the LEDs. In an actual embodiment of the present invention, the voltage source provided at node 322 is selected such that the voltage delivered to the LEDs 302, 304 in the circuit 300 is insufficient to cause the LEDs to generate a signal. The properties of operating an LED below a turn on voltage are well known in the relevant art and will not be described in greater detail. In an illustrative embodiment of the present invention, the voltage source may be 3.3 Volts. However, one skilled in the relevant art will appreciate that additional voltages may be utilized in combination to resistor values at node 320.

With the branch of the switches corresponding to the LED drive connected and the operational amplifier shut down, a voltage from the node 322 passes through the switches 312, 314 and to the information processing component 310. The resulting voltage can be read at node 320, which corresponds to the value of the voltage source minus the voltage drop across a resistor at node 322. This corresponds to the value generated by the information transmission component 310. The value detected at 320 can be transmitted to a microprocessor (not shown) for further processing as described above.

Figure 4:
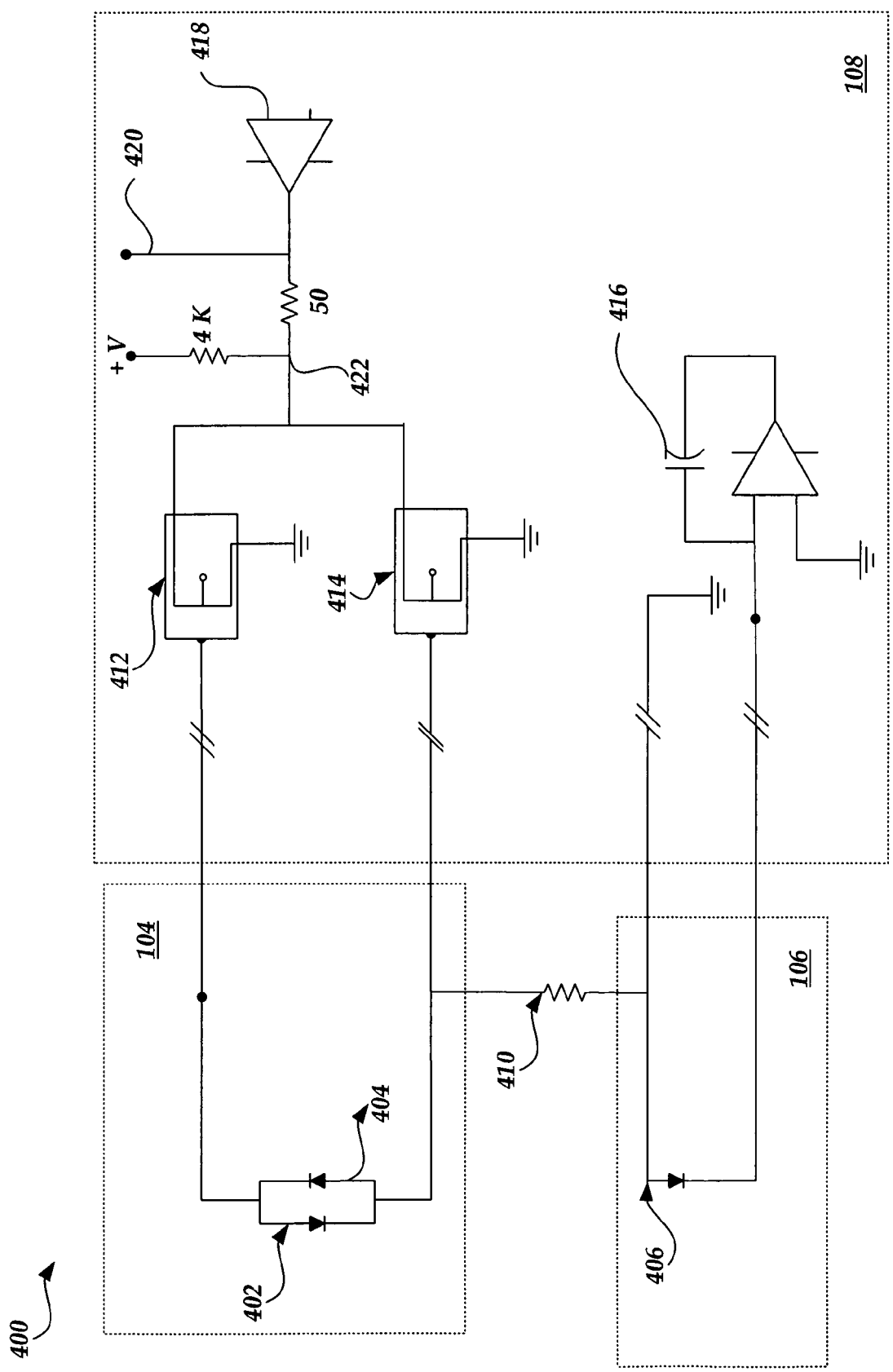
FIG. 4 is a circuit diagram implemented with a pulse oximeter system for measuring arterial oxygen saturation levels in a medium in accordance with the present invention.

In an alternative embodiment of the present invention, the information transmission component 310 may be a passive component having a resistivity corresponding to information to be processed by the pulse oximeter system 100. FIG. 4 is a circuit diagram of a circuit 400 illustrating the substitution of a passive component as the information transmission component 410. As illustrated in FIG. 4, the remaining components of the circuit 400 are identical to the circuit components of the circuit 300 illustrated with regard to circuit 300 (FIG. 3). Further, the operation of the circuit 400 to obtain the information from the information transmission component 410 does not vary from the procedure to obtain information from the information transmission component 310 in circuit 300.

In accordance with an illustrative embodiment of the present invention, the pulse oximeter system 100 may be included as part of an integrated medical information processing system in which multiple components are configured for patient monitoring. In accordance with this embodiment, the pulse oximeter system 100 communicates with other components in the integrated system via a common communication protocol. Further, to facilitate component interoperability, the pulse oximeter system components may be connected via a common cable and connectors that are not specific to the pulse oximeter system components. Because the integrated system utilizes common communication protocols and connectors, any number of processing components may be configured to collect specific data. Other modules that may be included with the pulse oximeter system 100 includes, but are not limited to, sleep recorder modules, body position modules, ECG signal detector modules, respiratory effort modules, motion detection modules, pressure/flow detection modules, and other monitoring modules.

While illustrative embodiments of the invention have been illustrated and described, it will be appreciated that various changes can be made therein without departing from the spirit and scope of the invention.

The embodiments of the invention in which an exclusive property or privilege is claimed are defined as follows:

1. A pulse oximeter for measuring arterial oxygen saturation levels comprising:
   an LED signal generator for transmitting one or more light signals to a testing medium when a turn on voltage is applied to the LED signal generator;
   a photodetector signal generator for obtaining at least a portion of the light signal generated by the LED signal generator and for generating a photocurrent corresponding to the detected signals;
   an integrated information transmission component for storing information corresponding to the pulse oximeter and for transmitting the information; and
   an oximeter processing system for applying a turn on voltage to the LED signal generator to cause the LED signal generator to generate a signal, for processing the photocurrent from the photodetector signal generator and for providing a voltage source to cause the information transmission component to transmit the stored information corresponding to the pulse oximeter;
   wherein the voltage of the voltage source provided by the oximeter processing system to cause the information transmission component to transmit the stored information is higher than the turn on voltage of the LED signal generator and is applied to the information transmission component without causing the LED signal generator to generate a signal.

2. The pulse oximeter as recited in claim 1, wherein the integrated information transmission component includes an identification chip for storing the information corresponding to the pulse oximeter.

3. The pulse oximeter as recited in claim 1, wherein the integrated information transmission component includes a passive circuit component for storing the information corresponding to the pulse oximeter.

4. The pulse oximeter as recited in claim 1, wherein information corresponding to the pulse oximeter includes information corresponding to characteristics of one or more components of the pulse oximeter.

5. The pulse oximeter as recited in claim 1, wherein the information corresponding to the pulse oximeter includes information corresponding to the operation of the pulse oximeter.

6. The pulse oximeter as recited in claim 1, wherein the information corresponding to the pulse oximeter is selected from a group consisting of a precise wavelength of a LED, a date of manufacture of a component, an identification of a manufacturer, authentication codes for a component, a serial number of a component, software programs, software updates, a patient identification number, and a clinic identification number.

7. The pulse oximeter as recited in claim 1, wherein the integrated information transmission component is configured to not require additional wiring to be integrated in the pulse oximeter.

8. A pulse oximeter for measuring arterial oxygen saturation levels comprising:
   means for transmitting one or more light signals to a testing medium in response to a turn on voltage;
   means for obtaining at least a portion of the light signal transmitted by the transmitting means and for generating a photocurrent corresponding to the detected signals;
   means for storing information corresponding to the pulse oximeter; and
   means for providing a voltage source to cause the information transmission component to transmit the stored information corresponding to the pulse oximeter, wherein the voltage of the voltage source to cause the information transmission component to transmit the stored information is higher than the turn on voltage of the means for transmitting one or more light signals to a testing medium.

9. The pulse oximeter as recited in claim 8, wherein the means for storing information corresponding to the pulse oximeter includes an identification chip for storing the information corresponding to the pulse oximeter.

10. The pulse oximeter as recited in claim 8, wherein the means for storing information corresponding to the pulse oximeter includes a passive circuit component for storing the information corresponding to the pulse oximeter.

11. The pulse oximeter as recited in claim 8, wherein information corresponding to the pulse oximeter includes information corresponding to characteristics of one or more components of the pulse oximeter.

12. The pulse oximeter as recited in claim 8, wherein the information corresponding to the pulse oximeter includes information corresponding to the operation of the pulse oximeter.

13. The pulse oximeter as recited in claim 8, wherein the information corresponding to the pulse oximeter is selected from a group consisting of a precise wavelength of the transmitting means, a date of manufacture of a component, an identification of a manufacturer, authentication codes for a component, a serial number of a component, software programs, software updates, a patient identification number, and a clinic identification number.

14. The pulse oximeter as recited in claim 8, wherein the means for storing information corresponding to the pulse oximeter is configured to not require additional wiring to be integrated in the pulse oximeter.

15. A pulse oximeter for measuring arterial oxygen saturation levels comprising:
- a signal generator for transmitting one or more signals to a testing medium when a turn on voltage is applied to the signal generator;
- a photodetector signal generator for processing at least a portion of the signal generated by the signal generator;
- an integrated information transmission component for storing information corresponding to the pulse oximeter and for transmitting the information, wherein the integrated information transmission component is configured to not require additional wiring to be integrated in the pulse oximeter; and
- an oximeter processing system in communication with the signal generator, the photodetector signal generator and the integrated information transmission component, wherein the oximeter processing system provides voltage to cause the information transmission component to transmit the stored information corresponding to the pulse oximeter, the voltage being higher than the turn on voltage of the signal generator and applied without causing the signal generator to generate a signal.

16. The pulse oximeter as recited in claim 15, wherein the integrated information transmission component includes an identification chip for storing the information corresponding to the pulse oximeter.

17. The pulse oximeter as recited in claim 15, wherein the integrated information transmission component includes a passive circuit component for storing the information corresponding to the pulse oximeter.

18. The pulse oximeter as recited in claim 15, wherein information corresponding to the pulse oximeter includes information corresponding to characteristics of one or more components of the pulse oximeter.

19. The pulse oximeter as recited in claim 15, wherein information corresponding to the pulse oximeter includes information corresponding to the operation of the pulse oximeter.

20. A pulse oximeter for measuring arterial oxygen saturation levels comprising:
- a light source for applying light at a selected wavelength to a test medium when a suitable turn on voltage is applied to the light source;
- a light detector for receiving at least a portion of the light produced by the light source and applied to the test medium, and generating a corresponding electrical signal;
- an integrated information transmission component for storing information related to the pulse oximeter and generating the information when a suitable voltage is applied to the integrated information component, the voltage being greater than the turn on voltage of the light source; and
- an oximeter processing system for (i) applying a turn on voltage to the light source, (ii) applying a voltage to the integrated information transmission component, (iii) processing the corresponding electrical signal generated by the light detector, and (iv) interpreting the corresponding electrical signal, the oximeter processing system including a switching system for controlling the application of the turn on voltage to the light source and the voltage to the integrated information transmission component such that when the voltage is applied to the integrated information transmission component, the light source is not turned on.

21. The pulse oximeter as recited in claim 20, wherein the integrated information transmission component includes an identification chip for storing the information corresponding to the pulse oximeter.

22. The pulse oximeter as recited in claim 20, wherein the integrated information transmission component includes a passive circuit component for storing the information corresponding to the pulse oximeter.

23. The pulse oximeter as recited in claim 20, wherein information related to the pulse oximeter includes information corresponds to characteristics of one or more components of the pulse oximeter.

24. The pulse oximeter as recited in claim 20, wherein the information related to the pulse oximeter includes information corresponds to the operation of the pulse oximeter.

25. The pulse oximeter as recited in claim 20, wherein the information related to the pulse oximeter is selected from a group consisting of the selected wavelength of the light applied by the light source to the test medium, a date of manufacture of a component, an identification of a manufacturer, authentication codes for a component, a serial number of a component, software programs, software updates, a patient identification number, and a clinic identification number.

26. The pulse oximeter as recited in claim 20, wherein the integrated information transmission component is configured to not require additional wiring to be integrated in the pulse oximeter.

* * * * *